United States Patent
Kato

(10) Patent No.: US 10,392,475 B2
(45) Date of Patent: *Aug. 27, 2019

(54) POLYAMIDE ELASTOMER, MEDICAL DEVICE, AND METHOD FOR PRODUCING POLYAMIDE ELASTOMER

(71) Applicant: KANEKA CORPORATION, Osaka-shi, Osaka (JP)

(72) Inventor: Takayuki Kato, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/573,754

(22) PCT Filed: May 11, 2016

(86) PCT No.: PCT/JP2016/064056
§ 371 (c)(1),
(2) Date: Nov. 13, 2017

(87) PCT Pub. No.: WO2016/182002
PCT Pub. Date: Nov. 17, 2016

(65) Prior Publication Data
US 2018/0148540 A1  May 31, 2018

(30) Foreign Application Priority Data

May 11, 2015 (WO) .................. PCT/JP2015/063529

(51) Int. Cl.
*C08G 69/40* (2006.01)
*A61M 25/00* (2006.01)
*A61M 25/10* (2013.01)

(52) U.S. Cl.
CPC ............. *C08G 69/40* (2013.01); *A61M 25/00* (2013.01); *A61M 25/10* (2013.01)

(58) Field of Classification Search
CPC ........ C08G 69/40; A61L 29/06; A61M 25/00; A61M 25/10; A61M 25/0043; A61M 2205/0216
USPC ....................................................... 528/310
See application file for complete search history.

(56) References Cited

U.S. PATENT DOCUMENTS

| | | | | |
|---|---|---|---|---|
| 4,218,351 A * | 8/1980 | Rasmussen | ............ | C08G 69/26 528/326 |
| 4,345,052 A | 8/1982 | Mumcu et al. | | |
| 4,345,064 A | 8/1982 | Mumcu | | |
| 5,574,128 A | 11/1996 | Judas et al. | | |
| 9,139,693 B2 * | 9/2015 | Takeo | ................... | C08G 69/40 |
| 9,555,604 B2 * | 1/2017 | Irisa | ...................... | C08G 69/36 |
| 10,188,908 B2 * | 1/2019 | Sullivan | ............. | A63B 37/0039 |
| 2003/0144462 A1 * | 7/2003 | Okushita | ................ | C08G 69/40 528/310 |
| 2009/0274913 A1 * | 11/2009 | Okushita | ................. | B32B 27/08 428/423.5 |
| 2011/0014833 A1 | 1/2011 | Hagiwara et al. | | |
| 2017/0349744 A1 * | 12/2017 | Chang | .................. | C08G 63/672 |
| 2018/0066109 A1 * | 3/2018 | Kato | ...................... | C08G 69/40 |
| 2018/0371166 A1 * | 12/2018 | Sudo | ....................... | C08G 69/00 |

FOREIGN PATENT DOCUMENTS

| | | | |
|---|---|---|---|
| JP | S45-7559 B1 | 3/1970 | |
| JP | 59-131628 A | 7/1984 | |
| JP | 59-193923 A | 11/1984 | |
| JP | 60-158221 A | 8/1985 | |
| JP | 2010-285703 A | 12/2010 | |
| WO | WO 2007/145324 A1 | 12/2007 | |
| WO | WO 2008/123450 A1 | 10/2008 | |
| WO | WO 2009/057805 A1 | 5/2009 | |
| WO | WO 2009/139087 A1 | 11/2009 | |
| WO | WO-2009139087 A1 * | 11/2009 | ............. C08G 69/40 |
| WO | WO 2012/132084 A1 | 10/2012 | |

OTHER PUBLICATIONS

International Search Report, issued in PCT/JP2016/064056, PCT/ISA/210, dated Jul. 26, 2016.
Written Opinion of the International Searching Authority, issued in PCT/JP2016/064056, PCT/ISA/237, dated Jul. 26, 2016.
Applicant brings to the attention of the Examiner the existence of copending U.S. Appl. No. 15/808,477 by the same Inventor/Applicant as in the present case (Takayuki Kato/Kaneka Corporation), filed Nov. 9, 2017, and which is the national stage of PCT/JP2016/064055, which was filed on May 11, 2016, and was published as WO 2016/182001 A1 on Nov. 17, 2016.
Extended European Search Report for Application No. 16792727.6 dated Jan. 2, 2019.

* cited by examiner

*Primary Examiner* — Douglas J McGinty
(74) *Attorney, Agent, or Firm* — Birch, Stewart, Kolasch & Birch, LLP

(57) ABSTRACT

A polyamide elastomer comprising a reaction product of components (a), (b), and (c). Component (a) has the formula HOOC—$R_1$—(—NH—CO—$R_1$-)$_n$—$NH_2$ (where each $R_1$ independently is linear saturated hydrocarbon, n represents a real number of 0 or greater, and when the formula contains multiple repeating units each containing $R_1$, n represents a total number of those repeating units) and the $M_n$ of component (a)=4000-10000. Component (b) has the formula HOOC—$R_2$—COOH (where $R_2$ represents a direct bond or a linear saturated hydrocarbon group). Component (c) has the formula $H_2N$—$R_4$—(—O—$R_4$-)$_m$—NH2 (where each $R_4$ independently represents a saturated hydrocarbon group containing 1 or more carbon atoms; m represents a real number of 1 or more; and when the formula contains two or more types of the repeating units each containing $R_4$, m represents a total number of the two or more types of the repeating units each containing $R_4$).

12 Claims, No Drawings

POLYAMIDE ELASTOMER, MEDICAL DEVICE, AND METHOD FOR PRODUCING POLYAMIDE ELASTOMER

TECHNICAL FIELD

The present invention relates to a polyamide elastomer, a medical device having the polyamide elastomer, and a method of producing the polyamide elastomer.

BACKGROUND ART

Polyamide elastomers are a resin compound that is widely used in various fields, such as packaging materials for food and the like; medical device members; members of electrical devices, machines, and precision instruments; and automobile members. The medical device members that are made of a polyamide elastomer include medical tubes and catheter balloons. For use in production of such medical device members, a polyamide elastomer is required to have moldability, such as extrusion moldability and blow moldability, which is the ability of the polyamide elastomer to be formed precisely into a desired shape, and dynamical properties, such as elasticity, elongation at break, and strength at break, which are the ability of the polyamide elastomer to withstand potential destruction caused by pressure or bending force applied during use.

Patent Literature 1 discloses a block polyether amide that is obtained by condensation polymerization of a certain polyamide having a carboxy group on either end, a polyoxyalkylene having an amino group on either end and having an alkylene group containing 3 or more carbon atoms, and a certain diamine. Patent Literature 2 discloses a polyether amide that is obtained by polycondensation of a polyamide-forming monomer, a polyoxyalkylene having an amino group on either end and having an alkylene group containing 3 or more carbon atoms, a certain diamine, and a certain amount of dicarboxylic acid. The polyether amides of Patent Literatures 1 and 2 are likely to have a certain degree of elasticity and impact resistance. However, in the polyether amides with the compositions described in Patent Literatures 1 and 2, use of the polyether having an alkylene group containing 3 or more carbon atoms is not enough to attain sufficient mechanical strength, such as elasticity, elongation at break, and strength at break. Therefore, further improvement has been demanded.

Patent Literature 3 discloses a polyamide elastomer that is obtained by polymerization of (A) a polyamide-forming monomer selected from certain aminocarboxylic acid compounds and certain lactam compounds, (B) at least one diamine compound selected from polyether diamines having a polytetramethylene oxide (PTMO) skeleton, branched diamines, branched alicyclic diamines, and norbornane diamines, and (C) a certain dicarboxylic acid compound. All of the diamine compounds used in the invention described in Patent Literature 3, however, have poor reactivity and thereby take a long time for polymerization. This may cause partial thermal cracking of the polymerization product during polymerization. This induces coloration of the resulting elastomer and causes insufficient progression of the reaction of the diamine compounds, impairing the strength characteristics of the resulting elastomer, such as elongation at break and strength at break.

Patent Literature 4 discloses a polyether-polyamide copolymer resin that has an elongation at break of 1000% or higher and a modulus of elasticity of 15 MPa or lower and is for use in coating of or impregnation into flexible fabric. This patent literature discloses a specific embodiment, which is a polyether polyamide resin obtainable by binding a soft segment and a hard segment together. The soft segment consists of a polyether polyamide that is composed of a polyether diamine compound having a $C_{2-3}$ alkylene group and a certain dicarboxylic acid compound. The hard segment consists of a polyamide that is composed of a certain aminocarboxylic acid and/or a certain lactam compound. Here, the polyether component of the polyether polyamide resin described in Patent Literature 4 has poor reactivity, so that the resin strength at break is insufficient.

CITATIONS LIST

Patent Literatures

Patent Literature 1: JP S59-193923 A
Patent Literature 2: JP S59-131628 A
Patent Literature 3: WO 2007/145324 A1
Patent Literature 4: WO 2009/139087 A1

SUMMARY OF INVENTION

Technical Problems

In view of the above problems, an object of the present invention is to provide a polyamide elastomer that is excellent in mechanical strength properties in a solid state, such as elasticity, elongation at break, and strength at break; excellent in extrusion moldability in a molten state; and excellent in moldability in a solid state, such as blow moldability.

Solutions to Problems

The inventor of the present invention has conducted intensive research to achieve the object described above, and thus completed the present invention. The present invention relates to a polyamide elastomer according to any one of [1] to [6] below, a medical device according to any one of [7] and [8] below, and a production method according to any one of [9] to [11] below.

[1] A polyamide elastomer is a reaction product of at least components (a), (b), and (c), the component (a) having a number average molecular weight of 4000 or higher and 10000 or lower.

The component (a) is at least one compound represented by formula (1):

[Formula 1]

$$\text{HOOC}-R_1-(\text{NH}-\text{CO}-R_1-)_n\text{NH}_2 \qquad (1)$$

In the formula (1), each $R_1$ independently represents a linear saturated hydrocarbon group containing 1 or more carbon atoms; n represents a real number of 0 or greater; and when the formula contains two or more types of repeating units each containing $R_1$, n represents a total number of the two or more types of the repeating units each containing $R_1$.

The component (b) is at least one compound represented by formula (2).

[Formula 2]

$$\text{HOOC}-R_2-\text{COOH} \qquad (2)$$

In the formula (2), $R_2$ represents a direct bond or a linear saturated hydrocarbon group containing 1 or more carbon atoms.

The component (c) is at least one compound represented by formula (3):

[Formula 3]

$$H_2N-R_4-(O-R_4)_m-NH_2 \quad (3)$$

In the formula (3), each $R_4$ independently represents a saturated hydrocarbon group containing 1 or more carbon atoms; m represents a real number of 1 or greater; and when the formula contains two or more types of repeating units each containing $R_4$, m represents a total number of the two or more types of the repeating units each containing $R_4$.

[2] The polyamide elastomer according to [1] is a reaction product of at least the components (a) to (c) and a component (d). The component (d) is at least one compound represented by formula (4).

[Formula 4]

$$H_2N-R_3-NH_2 \quad (4)$$

In the formula (4), $R_3$ represents a saturated hydrocarbon group containing 1 or more carbon atoms.

[3] In the polyamide elastomer according to [1] or [2], wherein the component (c) is a component (c1). The component (c1) is at least one compound represented by formula (5)

[Formula 5]

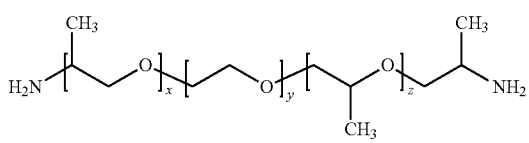

(5)

In the formula (5), (x+z) represents a real number of 1 or greater and 6 or smaller; and y represents a real number of 1 or greater and 20 or smaller.

[4] In the polyamide elastomer according to any one of [1] to [3], the component (d) is at least one aliphatic diamine selected from ethylenediamine, trimethylenediamine, tetramethylenediamine, hexamethylenediamine, undecamethylenediamine, dodecamethylenediamine, and 2,2-4/2,4,4-trimethylhexamethylenediamine.

[5] In the polyamide elastomer according to any one of [1] to [4], a molar ratio (AB) of amino groups in the component (a) (represented by (A)) to monocarboxyl groups in the component (b) (represented by (B)) is substantially 1/1.

[6] The polyamide elastomer according to any one of [1] to [5] contains phosphorus compound in a manner of containing element phosphorus in an amount of 5 ppm or higher and 5000 ppm or lower.

[7] A medical device has a member that is made by using the polyamide elastomer as described in any one of [1] to [6].

[8] In the medical device according to [7], the member is a catheter balloon or a medical tube.

[9] A method of producing a polyamide elastomer as described in any one of [1] to [6], the method includes:
step (i) of allowing the component (a) and the component (b) to react, thereby obtaining a prepolymer; and
step (ii) of mixing the prepolymer with the component (c) to react with each other.

[10] In the method of producing a polyamide elastomer according to [9], the prepolymer is mixed with the component (c) and the component (d) to react with each other.

[11] In the method of producing a polyamide elastomer according to [9] or [10], each of the components in at least the steps (i) and (ii) is caused to react by a melt kneading method.

[12] The method of producing a polyamide elastomer according to any one of [9] to [11], further includes adding a phosphorus compound in at least one of the steps (i) and (ii) in an amount of 10 ppm or higher and 10000 ppm or lower relative to the total amount of the components (a) to (c) or the total amount of the components (a) to (d).

Advantageous Effects of Invention

The present invention makes it possible to obtain a polyamide elastomer that is excellent in dynamical properties in a solid state, such as elasticity, elongation at break, and strength at break; excellent in extrusion moldability in a molten state; and excellent in moldability in a solid state, such as blow moldability.

DESCRIPTION OF EMBODIMENTS

Embodiments of a polyamide elastomer of the present invention are described below. The scope of the present invention is not limited to these embodiments.

The polyamide elastomer of the present invention is a reaction product of at least components (a), (b), and (c). In other words, the polyamide elastomer of the present invention has structures derived from at least the components (a), (b), and (c). The component (a) has a number average molecular weight of 4000 or higher and 10000 or lower. Accordingly, such certain components (a) to (c) are used and the certain range of the number average molecular weight of component (a) is achieved, in other words, the structure derived from such certain component (a) having a number average molecular weight of 4000 or more and 10000 or lower and the structures derived from such certain components (b) and (c) are used, thereby attaining the effects of the present invention. The polyamide elastomer of the present invention has a hard segment that is a polyamide structural unit derived from the component (a) and/or a polyamide structural unit derived from a reaction product of the components (b) and (c); and a soft segment that is a polyether structural unit derived from the component (c). When the component (a) having a number average molecular weight within the certain range is bonded to the component (c) via the component (b) to form a structural unit, the resulting polymerization reactivity may be excellent because of the suitable balance between the length of the hard segment and the length of the soft segment, leading to further enhancement in elongation at break and strength at break of the resulting polyamide elastomer.

Next, the components (a) to (c) and the polyamide elastomer of the present invention will be described in more detail.

The component (a) used in the present invention is at least one compound represented by formula (1).

[Formula 6]

$$HOOC-R_1-(NH-CO-R_1)_n-NH_2 \quad (1)$$

In formula (1), each $R_1$ represents the same linear saturated hydrocarbon group containing 1 or more carbon atoms or independently represents a linear saturated hydrocarbon group containing 1 or more carbon atoms; n represents a real number of 0 or greater; and when the formula contains two or more types of repeating units each containing $R_1$, n represents the total number of the two or more types of the repeating units each containing $R_1$. From the viewpoints of polymerization reactivity and dynamical properties of the resulting polyamide elastomer, it is preferable that n be 1 or greater and 100 or smaller, more preferably 10 or greater and 80 or smaller, further preferably 18 or greater and 77 or smaller. Here, n may be determined from a number average molecular weight that is obtained by gel permeation chromatography (GPC).

The $R_1$ in the component (a) is simply required to be a saturated hydrocarbon group containing 1 or more carbon atoms. From the viewpoints of polymerization reactivity and dynamical properties of the resulting polyamide elastomer, it is preferable that $R_1$ be a saturated hydrocarbon group containing 6 or more and 18 or less carbon atoms. Preferable examples of the component (a) include aminocarboxylic acids such as 1- to 6-aminohexanoic acids, 1- to 7-aminoheptanoic acids, 1- to 8-aminooctanoic acids, 1- to 9-aminononanoic acids, 1- to 10-aminodecanoic acids, 1- to 11-aminoundecanoic acids, 1- to 12-aminododecanoic acids, 1- to 14-aminotetradecanoic acids, 1- to 16-aminohexadecanoic acids, 1- to 17-aminoheptadecanoic acids, and 1- to 18-aminooctadecanoic acids, and condensation products thereof. When the component (a) is a condensation product of aminocarboxylic acid, the condensation product may be either derived from one type of aminocarboxylic acid or two or more types of aminocarboxylic acid.

The toughness of the resulting polyamide elastomer tends to be enhanced as the carbon chain of $R_1$ becomes longer, in particular.

The component (a) has a number average molecular weight of 4000 or higher and 10000 or lower, preferably 5000 or higher and 7000 or lower, more preferably 5000 or higher and 6000 or lower.

With the number average molecular weight being within this range, the mechanical properties of the resulting block copolymer are excellent.

The number average molecular weight of the component (a) may be determined by gel permeation chromatography (GPC), for example. It is known that the number average molecular weight thus measured varies about 10%. Therefore, when GPC is adopted to determine the number average molecular weight in the present invention, the average value of a plurality of measurements is used as the number average molecular weight. When multiple measurements cannot be carried out, it is checked whether there is an overlap between the above range and the number average molecular weight obtained by a single measurement±about 10%. When these two ranges overlap each other, it is considered that the above conditions of the number average molecular weight of the component (a) of the present invention are satisfied.

The component (b) used in the present invention is at least one compound represented by formula (2).

[Formula 7]

HOOC—$R_2$—COOH  (2)

In formula (2), $R_2$ represents a direct bond or a linear saturated hydrocarbon group containing 1 or more carbon atoms.

The linear saturated hydrocarbon group is not particularly limited as long as it contains 1 or more carbon atoms. From the viewpoints of polymerization reactivity and dynamical properties of the resulting polyamide elastomer, it is preferable that the linear saturated hydrocarbon group contain 2 or more and 10 or less carbon atoms.

Specific examples of the compounds usable as the component (b) include, but not limited to, dicarboxylic acids such as oxalic acid, malonic acid, succinic acid, glutaric acid, adipic acid, pimelic acid, suberic acid, azelaic acid, and sebacic acid. Only one type of the dicarboxylic acids may be used, or two or more types of the dicarboxylic acids may be used.

The component (c) used in the present invention is at least one compound represented by formula (3).

[Formula 8]

$$H_2N\text{—}R_4\text{—}(O\text{—}R_4)_m\text{—}NH_2 \quad (3)$$

In formula (3), each $R_4$ represents the same saturated hydrocarbon group containing 1 or more carbon atoms or independently represents a saturated hydrocarbon group containing 1 or more carbon atoms; m represents a real number of 1 or greater; and when the formula contains two or more types of repeating units each containing $R_4$, m represents the total number of the two or more types of the repeating units each containing $R_4$. In formula (5) below, for example, $m = x+y+z$.

The saturated hydrocarbon group is not particularly limited as long as it contains 1 or more carbon atoms. From the viewpoint of excellent elasticity, it is preferable that the saturated hydrocarbon group contain 1 or more and 10 or less carbon atoms, more preferably 2 or more and 4 or less carbon atoms. The saturated hydrocarbon group may have either a linear structure or a branched structure.

From the viewpoint of excellent reactivity, it is preferable that the component (c) of the present invention be a component (c1).

The component (c1) used in the present invention is at least one compound represented by formula (5).

[Formula 9]

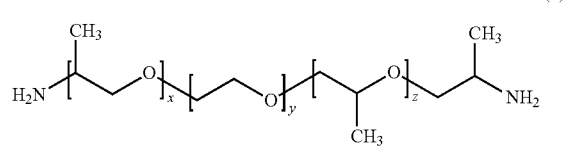

(5)

Regarding x, y, and z in formula (5), (x+z) represents a real number of 1 or greater and 6 or smaller and y represents a real number of 1 or greater and 20 or smaller. With these values being within these ranges, an excellent balance between polymerization reactivity and elasticity may be attained. It is preferable that (x+z) be 1 or greater and 5 or smaller, further preferably 1 or greater and 3.8 or smaller. It is preferable that y be 1 or greater and 15 or smaller, more preferably 1 or greater and 9.2 or smaller. Here, x, y, and z may be determined by GPC measurement as described, for example, in examples below.

The component (c1) may be, for example, a polyether diamine compound that is an amino-modified form of polyoxyethylene, 1,2-polyoxypropylene, 1,3-polyoxypropylene, or a polyoxyalkylene that is a copolymer of these. More specifically, Jeffamine ED products manufactured by Huntsman Corporation (U.S.) are preferable, for example. Among these products, Jeffamine ED600 and ED900 each have a value of (x+z) in formula (4) of 1 or greater and 6 or smaller and a value of y in the same formula of 1 or greater and 20 or smaller. More specifically, ED900 has a value of (x+z) of 1 or greater and 6 or smaller; ED600 has a value of (x+z) of 1 or greater and 3.8 or smaller; ED900 has a value of y of 1 or greater and 15 or smaller; and ED600 has a value of y of 1 or greater and 9.2 or smaller. It is preferable that ED600 and ED900, each having a value of (x+z) and a value of y within the above ranges, have number average molecular weights ranging from 500 to 700 and from 800 to 1000, respectively. Each of these number average molecular weights is the numerical value calculated from the proton ratio that is obtained by nuclear magnetic resonance using deuterated chloroform solvent.

Examples of more preferable embodiments of the polyamide elastomer that is a reaction product of at least the components (a) to (c) described above, in other words, more preferable embodiments of the polyamide elastomer having the structures derived from at least the certain components (a) to (c) include embodiments attributable to reaction of the components (a) to (c) of Nos. 1 to 16 shown in Table 1, in other words, include embodiments that have structures derived from various combinations of the components (a) to (c) of Nos. 1 to 16 shown in Table 1.

Since excellent mechanical strength of the resulting polyamide elastomer is obtained as long as the number average molecular weight of the component (a) is within a predetermined range, not only the components (a) to (c) but also the component (d) may be subjected to reaction in the present invention. More specifically, the polyamide elastomer of the present invention may be a reduction product of at least the components (a), (b), (c), and (d), in other words, the polyamide elastomer of the present invention may have structures derived from at least such certain components (a) to (d).

The component (d) used in the present invention is at least one compound represented by formula (4).

[Formula 10]

$$H_2N-R_3-NH_2 \tag{4}$$

In formula (4), $R_3$ represents a saturated hydrocarbon group containing not less than 1 carbon atom.

$R_3$ is not limited as long as it is a linear or branched saturated hydrocarbon group containing 1 or more carbon atoms. From the viewpoint of further enhancing the dynami-

TABLE 1

| No. | Component (a) | Component (b) | Component (c) |
|---|---|---|---|
| 1 | 6-Aminohexanoic acid (number of carbon atoms: 6) | Succinic acid (number of carbon atoms: 4) | Polyether diamine $3.8 \geq x + z \geq 1$, $9.2 \geq y \geq 1$ $700 \geq Mn \geq 500$ |
| 2 | (a polymer satisfying $77 \geq n \geq 30$) | | Polyether diamine $6.2 \geq x + z \geq 1$, $13 \geq y \geq 1$ $1000 \geq Mn \geq 800$ |
| 3 | | Adipic acid (number of carbon atoms: 6) | Polyether diamine $3.8 \geq x + z \geq 1$, $9.2 \geq y \geq 1$ $700 \geq Mn \geq 500$ |
| 4 | | | Polyether diamine $6.2 \geq x + z \geq 1$, $13 \geq y \geq 1$ $1000 \geq Mn \geq 800$ |
| 5 | | Sebacic acid (number of carbon atoms: 10) | Polyether diamine $3.8 \geq x + z \geq 1$, $9.2 \geq y \geq 1$ $700 \geq Mn \geq 500$ |
| 6 | | | Polyether diamine $6.2 \geq x + z \geq 1$, $13 \geq y \geq 1$ $1000 \geq Mn \geq 800$ |
| 7 | | Dodecanedioic acid (number of carbon atoms: 12) | Polyether diamine $3.8 \geq x + z \geq 1$, $9.2 \geq y \geq 1$ $700 \geq Mn \geq 500$ |
| 8 | | | Polyether diamine $6.2 \geq x + z \geq 1$, $13 \geq y \geq 1$ $1000 \geq Mn \geq 800$ |
| 9 | 12-Aminododecanoic acid (number of carbon atoms: 12) | Succinic acid (number of carbon atoms: 4) | Polyether diamine $3.8 \geq x + z \geq 1$, $9.2 \geq y \geq 1$ $700 \geq Mn \geq 500$ |
| 10 | (a polymer satisfying $47 \geq n \geq 18$) | | Polyether diamine $6.2 \geq x + z \geq 1$, $13 \geq y \geq 1$ $1000 \geq Mn \geq 800$ |
| 11 | | Adipic acid (number of carbon atoms: 6) | Polyether diamine $3.8 \geq x + z \geq 1$, $9.2 \geq y \geq 1$ $700 \geq Mn \geq 500$ |
| 12 | | | Polyether diamine $6.2 \geq x + z \geq 1$, $13 \geq y \geq 1$ $1000 \geq Mn \geq 800$ |
| 13 | | Sebacic acid (number of carbon atoms: 10) | Polyether diamine $3.8 \geq x + z \geq 1$, $9.2 \geq y \geq 1$ $700 \geq Mn \geq 500$ |
| 14 | | | Polyether diamine $6.2 \geq x + z \geq 1$, $13 \geq y \geq 1$ $1000 \geq Mn \geq 800$ |
| 15 | | Dodecanedioic acid (number of carbon atoms: 12) | Polyether diamine $3.8 \geq x + z \geq 1$, $9.2 \geq y \geq 1$ $700 \geq Mn \geq 500$ |
| 16 | | | Polyether diamine $6.2 \geq x + z \geq 1$, $13 \geq y \geq 1$ $1000 \geq Mn \geq 800$ | cal properties of the resulting polyamide elastomer, it is preferable that 2 or more and 14 or less carbon atoms be contained, more preferably 4 or more and 12 or less carbon atoms be contained. Specific examples include, but not limited to, aliphatic diamines such as ethylenediamine, trimethylenediamine, tetramethylenediamine, pentamethylenediamine, hexamethylenediamine, heptamethylenediamine, octamethylenediamine, nonamethylenediamine, decamethylenediamine, undecamethylenediamine, dodecamethylenediamine, 2,2-4/2,4,4-trimethylhexamethylenediamine, and 3-methylpentamethyldiamine. More preferable among these from the same viewpoint as above is at least one aliphatic diamine selected from hexamethylenediamine, heptamethylenediamine, octamethylenediamine, nonamethylenediamine, decamethylenediamine, undecamethylenediamine, and dodecamethylenediamine.

The molar ratio of the component (d), when used, to the component (c) in the present invention is not particularly limited. From the viewpoint of imparting excellent workability and excellent mechanical properties to the resulting polyamide elastomer, it is preferable that the molar ratio (d/c) of the component (d) to the component (c) range from 8/2 to 1/9, more preferably from 7/3 to 2/8, further preferably from 6/4 to 3/7. This molar ratio may be determined from the amount of protons in the α-carbons adjacent to the terminal amine groups and the amount of protons in the α-carbons adjacent to the ether groups, all measured by nuclear magnetic resonance (NMR). During production, this molar ratio corresponds to the molar ratio between the components used.

The molar ratio (AB) of amino groups in the component (a) (represented by (A)) to monocarboxyl groups in the component (b) (represented by (B)) is not particularly limited in the present invention, but is preferably 1/2 or higher and 5/4 or lower, more preferably and substantially be 1/1 for easy obtainment of a polyamide elastomer with a preferable number average molecular weight. The molar ratio being substantially 1/1 means that the number of moles of amino groups and the number of moles of monocarboxyl groups, which are calculated from the weight of the raw material, are approximately the same with each other.

It is preferable that the polyamide elastomer of the present invention have a melt viscosity (melt flow rate, MFR) ranging from 0.1 to 20 g/10 min at 230° C. and 2.16 kgf (21.2 N). With the melt viscosity being within this range, excellent extrusion moldability is obtained. The melt viscosity within this range may be attained by appropriate adjustment of the polymerization reaction temperature, the reaction time, and the concentration of the solution, for example.

It is preferable that the polyamide elastomer of the present invention have a Shore (D) hardness ranging from 50 to 100, more preferably from 60 to 80. With the Shore (D) hardness being within this range, the resulting formed article has elasticity. The Shore (D) hardness within this range may be attained by appropriate adjustment of the amount of the component (c) to feed, or by appropriate adjustment of the ratio of the component (c) to the component (d) to feed when the component (d) is used.

It is preferable that the polyamide elastomer of the present invention have a number average molecular weight of 10000 or higher and not 150000 or lower, more preferably 20000 or higher and 100000 or lower. With the number average molecular weight being within this range, excellent workability and excellent mechanical properties are obtained.

It is preferable that a molded article made of the polyamide elastomer of the present invention have an elongation at break of 100% or higher and 600% or lower, more preferably 200% or higher and 600% or lower, measured in a tensile test; and a stress at break of 20 MPa or higher and 100 MPa or lower, more preferably 30 MPa or higher and 90 MPa or lower. The tensile test may be carried out by a method described below, for example.

The polyamide elastomer of the present invention may contain a phosphorus compound. With a phosphorus compound contained therein, the elongation at break and the stress at break of the resulting molded article may be further enhanced and such a molded article is suitable for use to make medical balloons, for example. In addition, potential coloration caused by stabilization of the polymerization reaction and by oxidation during production of the polyamide elastomer may be prevented, as described below. Examples of the phosphorus compound include phosphoric acid, pyrophosphoric acid, polyphosphoric acid, phosphorous acid, hypophosphorous acid, and alkali metal salts and alkaline-earth metal salts thereof. Among them, phosphorous acid, hypophosphorous acid, and alkali metal salts and alkaline-earth metal salts thereof are preferable from the viewpoints of enhancing polymerization reaction stability, imparting thermal stability to the resulting polyamide elastomer, and enhancing the dynamical properties of the resulting molded article.

It is preferable that the content of the phosphorus compound be 5 ppm or higher and 5000 ppm or lower, more preferably 20 ppm or higher and 4000 ppm or lower, further preferably 30 ppm or higher and 3000 ppm or lower in terms of the content of the element phosphorus.

In addition to the phosphorus compound, various additives may also be contained in the polyamide elastomer of the present invention for various purposes, as long as the properties of the polyamide elastomer of the present invention are not impaired. More specifically, a heat-resistant agent, an ultraviolet absorber, a light stabilizer, an antioxidant, an antistatic agent, a lubricant, a slip agent, a nucleating agent, a tackifier, a mold release agent, a plasticizer, a pigment, a dye, a flame retardant, a reinforcing agent, an inorganic filler, a microfilament, and an x-ray opaque agent may be contained, for example.

Next, embodiments of a method of producing a polyamide elastomer of the present invention will be described. The scope of the present invention is not limited to these embodiments.

The polyamide elastomer of the present invention is obtainable by reaction of at least the components (a); (b); and (c), and (d) used depending on the necessity. Examples of the method include a method of simultaneously mixing the components (a) to (c), or simultaneously mixing the components (a) to (d) to cause reaction; and a method of allowing the component (a) to react with the component (b), and then adding the other components thereto to cause further reaction. From the viewpoint of efficiently synthesizing a block copolymer that has a desired hard segment and a desired soft segment, it is preferable to select, among these methods, a method that has step (i) of mixing the components (a) and (b) to cause reaction to obtain a prepolymer (hereinafter, called "step (i)"); and a step of mixing the prepolymer obtained in step (i) and the component (c) or the components (c) and (d) to cause reaction (hereinafter, called "step (ii)").

The ratio between the components (a) and (b) mixed in step (i) is not particularly limited. In order to easily obtain a hard segment with a desired length, it is preferable that the molar ratio (AB) of amino groups in the component (a) (represented by (A)) to monocarboxyl groups in the component (b) (represented by (B)) be 1/2 or higher and 5/4 or lower, more preferably and substantially be 1/1.

In either of the method involving simultaneous mixing of the component (a) to (c) or the components (a) to (d) or the method having steps (i) and (ii), it is preferable that the total number of moles of amino groups in the component (a) to the component (c) or the components (a) to (d) be substantially the same as the number of moles of carboxyl groups in these components.

When using a compound that potentially disturbs the equimolar balance between the amino groups and the carboxyl groups in the method of producing a polyamide elastomer of the present invention, it is desirable that the amount of the compound be low enough not to impair desired physical properties.

The ratio between the components (a) to (c) mixed in the method of producing a polyamide elastomer of the present invention is not particularly limited. It is preferable that the ratio of the component (a) to the total of the components (a) to (c) range from 70 to 98.5 weight %, more preferably from 85 to 98 weight %; it is preferable that the ratio of the component (b) to the total of the components (a) to (c) range from 0.5 to 20 weight %, more preferably from 1 to 10 weight %; it is preferable that the ratio of the component (c) to the total of the components (a) to (c) range from 0.5 to 20 weight %, more preferably from 1 to 10 weight %. When the component (d) is used, the ratio between the components (a) to (d) mixed is not particularly limited but it is preferable that the ratio of the component (a) to the total of the components (a) to (d) range from 70 to 98.5 weight %, more preferably from 85 to 98 weight %; it is preferable that the ratio of the component (b) to the total of the components (a) to (d) range from 0.5 to 20 weight %, more preferably from 1 to 10 weight %; it is preferable that the ratio of the component (c) to the total of the components (a) to (d) range from 0.5 to 20 weight %, more preferably from 1 to 10 weight %; and it is preferable that the ratio of the component (d) to the total of the components (a) to (d) range from 0.5 to 30 weight %, more preferably from 1 to 20 weight %.

Accordingly, it is preferable to take step (ii) into consideration when determining the amounts of the components (a) and (b) to be mixed in step (i). In addition, it is preferable to take into consideration the molar ratio of amino groups to carboxyl groups contained in the total of the components (a) to (c) or the components (a) to (d), and it is preferable to determine the amounts of the components so that a substantial equimolar balance is successfully established between them, as described above. When the component (a) is a condensation polymerization product, the amounts of the components to be mixed may be determined based on the compounds to be subjected to the condensation polymerization.

The reactions in the steps (i) and (ii) in the method of producing a polyamide elastomer of the present invention may be carried out either in solvent or without solvent (namely, non-solvent reactions). For the purpose of easily obtaining a desired polyamide elastomer without purification or the like, it is preferable that the reactions be carried out without solvent (namely, non-solvent reactions). Such non-solvent reactions may be carried out by a melt kneading method. Therefore, it is preferable that the reaction of the components (a) and (b) in step (i) and the reaction of the prepolymer and the component (c) or the reaction of the prepolymer and the components (c) and (d) in step (ii) be carried out by a melt kneading method.

The polymerization reaction of the components (a) to (c) or the components (a) to (d) in the method of producing a polyamide elastomer of the present invention may be normal-pressure melt polycondensation reaction, vacuum melt polycondensation reaction, or a combination of these. When the vacuum melt polycondensation is adopted, it is preferable to set a pressure inside the reaction vessel from 0.1 to 0.01 MPa in a nitrogen gas atmosphere, from the viewpoint of polymerization reactivity. Any of the melt polycondensation reactions described above may be carried out by a melt kneading method without solvent.

The reaction temperature in the steps (i) and (ii) in the method of producing a polyamide elastomer of the present invention is not particularly limited, as long as the polymerization reaction occurs. From the viewpoint of the balance between the reaction rate and thermal cracking inhibition, it is preferable that the reaction temperature range from 160 to 300° C., more preferably from 200 to 280° C. The reaction temperature in the step (i) may be the same as or different from the reaction temperature in the step (ii).

For the purpose of attaining a high molecular weight and inhibiting coloration, for example, it is preferable that the polymerization reaction time in the steps (i) and (ii) in the method of producing a polyamide elastomer of the present invention range from 3 to 10 hours. The polymerization reaction time in the step (i) may be the same as or different from the polymerization reaction time in the step (ii).

The method of producing a polyamide elastomer of the present invention may be carried out either in a batch mode or in a continuous mode. For example, any of the following may be adopted: a batch mode that is carried out in a batch-mode reaction tank or the like; and a continuous mode that is carried out in a single-tank or multi-tank continuous reaction apparatus, a tubular-shape continuous reaction apparatus, or a combination of these apparatuses.

In the production of the polyamide elastomer of the present invention, a phosphorus compound may be used as a catalyst, as needed. Examples of the phosphorus compound include phosphoric acid, pyrophosphoric acid, polyphosphoric acid, phosphorous acid, hypophosphorous acid, and alkali metal salts and alkaline-earth metal salts thereof. Among these, an inorganic phosphorus compound such as phosphorous acid, hypophosphorous acid, and alkali metal salts and alkaline-earth metal salts thereof is preferable from the viewpoints of enhancing polymerization reaction stability, imparting thermal stability to the resulting polyamide elastomer, and enhancing the dynamical properties of the resulting molded article.

It is preferable that the amount (in terms of weight) of the phosphorus compound added in at least one of steps (i) and (ii) be 10 ppm or higher and 10000 ppm or lower, more preferably 100 ppm or higher and 5000 ppm or lower relative to the total weight of the components (a) to (c) or the total weight of the components (a) to (d) when the component (d) is used. At this time, if the component (a) is a condensation polymerization product, the amount of the phosphorus compound added may be determined based on the compounds to be subjected to the condensation polymerization. The weight of the phosphorus compound added may not be necessarily equivalent to the content of the element phosphorus in the resulting polyamide elastomer, since a partial amount of the phosphorus compound may be sometimes released from the reaction system in a form of a reaction by-product. It is preferable that the content of the element phosphorus in the resulting polyamide elastomer be 5 ppm or higher and 5000 ppm or lower, more preferably 20 ppm or higher and 4000 ppm or lower, further preferably 30 ppm or higher and 3000 ppm or lower.

After the reaction of the components in the step (ii) is completed, a string of the resulting molten polymer may be, for example, pulled out of the reaction system, cooled, and made into pellets or the like as needed.

The polyamide elastomer of the present invention contains appropriate amounts of polyether chain groups and polyamide groups. As a result, the polyamide elastomer of the present invention does not greatly change its physical properties when it absorbs water. In addition, the polyamide elastomer of the present invention has excellent extrusion moldability and excellent roll moldability resulting from the melt properties of the resin, excellent blow moldability, and excellent strength and toughness. Thus, the polyamide elastomer of the present invention may be usable for producing molded articles for use in various fields. For example, the polyamide elastomer of the present invention may be subjected to extrusion molding to produce a member such as a tube, a hose, and a medical tube, or the polyamide elastomer of the present invention may be subjected to blow molding to produce a bottle, a container, a catheter balloon, and so on.

The polyamide elastomer of the present invention is particularly suitable for use to produce a medical member used in a medical device. Examples of the medical member include catheter balloons and medical tubes.

Next, the medical member made by using the polyamide elastomer is described referring to the case in which the medical member is a catheter balloon. The scope of the present invention is, however, not limited to this case.

A catheter balloon (hereinafter, simply called "balloon") may be produced by making a tube (hereinafter, it may be called "parison") using the polyamide elastomer of the present invention and then subjecting the resulting parison to further processing.

The method of making a parison using the polyamide elastomer may be a typical, known molding method. Examples of the method include extrusion molding, injection molding, and melt spinning molding. The resulting parison is typically a cylinder with a uniform diameter in a long-axis direction.

The method of producing a balloon from the parison may be a typical, known molding method. For example, a blow molding method such as free blowing or mold blowing or a vacuum molding method may be employed to carry out biaxial stretching to prepare a balloon with a desired shape. The temperature during molding is typically from 95 to 165° C.

It is preferable that the rate of enlargement of the inner diameter of the parison when formed into a balloon be 400% or greater and 900% or smaller, more preferably 500% or greater and 800% or smaller. The rate of enlargement of the inner diameter in the present invention is calculated by the following expression.

Rate of enlargement of inner diameter (%)=((inner diameter of balloon when inflated during molding)/(inner diameter of parison))×100

The balloon produced in this way is subjected to examinations such as visual examination, and only after it has passed the examinations, the balloon is eligible to be used as a medical member for use in a medical device such as a balloon catheter. When the visual examination finds a rhombic mark, a fish eye, or a crack on the surface, the balloon is evaluated as defective.

As described above, the polyamide elastomer of the present invention is excellent at least in dynamical properties such as elasticity, elongation at break, and strength at break and also in workability such as extrusion moldability in a molten state and blow moldability in a solid state. Therefore, the polyamide elastomer of the present invention may be used in various applications, such as medical device members; packaging materials for food and the like; members of electrical devices, machines, and precision instruments; and automobile members.

EXAMPLES (Measurement of Melt Flow Rate)

A melt flow rate (MFR) was measured with a G-01 melt indexer (manufactured by Toyo Seiki Seisaku-sho, Ltd.) in accordance with ASTM-D3418. The resin sample was dried in an oven at 80° C. for 4 hours for the measurement.

(Measurement of Number Average Molecular Weight (Mn))

A number average molecular weight (Mn) was measured by gel permeation chromatography (GPC). The measurement by GPC was carried out using, as a GPC apparatus, a GPC unit manufactured by Shimadzu Corporation (an SCL-10Avp system controller, an LC-10ADvp pump, a CTO-10Avp column oven, and an RID-10A detector), an LF-404 column manufactured by SHODEX, and hexafluoroisopropanol as solvent. The molecular weight distribution thus obtained was used in combination with a calibration curve generated with the use of a reference standard (polymethyl methacrylate, PMMA) to determine the number average molecular weight in terms of PMMA.

The number average molecular weight thus measured varied about 10% and, therefore, the average value of two or three measurements was used.

(Tensile Test)

A tensile test was carried out using a specimen that was compliant with ASTM-D638 (TYPES). The specimen was prepared in the following way: a pellet of a polyamide elastomer obtained in an example or a comparative example was pressed with a Mini Test Press (manufactured by Toyo Seiki Seisaku-sho, Ltd.; trade name, MP-2FH) at 190° C., and then cooled; the resulting film with a thickness of 1 mm was subjected to die cutting with a die blade that was compliant with the above specification; and the resultant was dried at 80° C. for 4 hours. The tensile test was carried out at a rate of 200 mm/min.

(Measurement of Shore (D) Hardness)

A sheet with a thickness of 6 mm was subjected to Shore (D) measurement in accordance with ASTM-D2240 in a thermostatic chamber controlled at 23° C. The sheet with a thickness of 6 mm was prepared from a pellet of a polyamide elastomer obtained in an example or a comparative example with the same press machine as above. The measurement was carried out with a load tester for D type durometer manufactured by Kobunshi Keiki Co., Ltd.

(Quantitative Assessment of Remaining Element Phosphorus)

Each of polyamide elastomers obtained in Examples 10 and 11 was subjected to quantitative assessment of the element phosphorus contained therein.

Pretreatment was carried out in the following way: about 0.1 g of a sample was accurately weighed in a digestion vessel; thereto, sulfuric acid and nitric acid were added; and the resulting mixture was subjected to high-pressure acidolysis with the use of a microwave digestion system (manufactured by Milestone General K.K.; trade name, ETHOS One). The liquid obtained after digestion was diluted to 50 ml, which was subjected to quantitative assessment. The quantitative assessment was carried out by inductively coupled plasma (ICP) emission spectrophotometry (with an ICPS-8100 device manufactured by Shimadzu Corporation).

(Visual Examination of Formed Balloon)

A parison molded in an example was subjected to blow molding to obtain a balloon. The resulting balloon was visually examined on the surface with a 20-power loupe for any cracks with a size of 0.0005 mm$^2$ or greater.

(Measurement of Compressive Strength)

A pellet of a polyamide elastomer obtained in an example or a comparative example was made into a blow molded article. The resulting blow molded article was heat sealed on one side, followed by measurement with a burst leak tester (manufactured by Crescent Design, Inc.; trade name, MODEL 1000) in a water bath at 37° C.

Example 1

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. Then, polymerization was allowed to proceed until the number average molecular weight reached 4100. Thus, a component (a) was obtained, which was to be used as a hard segment.

To the resultant, 43.8 g (0.30 mol) of adipic acid as a component (b) was added the amount of which was equivalent to the number of moles of the terminal amine groups contained in the hard segment. Reaction was allowed to proceed at 220° C. for 1 hour for dicarboxylation of the hard segment (step (i)).

Thereto, 180 g (0.300 mol) of a polyether diamine (Jeffamine ED600 manufactured by Huntsman; having a value of (x+z) in formula (4) of 1 or greater and 3.8 or smaller and a value of y in the same formula of 1 or greater and 9.2 or smaller; and having a number average molecular weight ranging from 500 to 700) as a component (c1) were added, so as to have the total amount equivalent to the total number of moles of the terminal carboxyl groups present on both ends of the dicarboxylated hard segment obtained above. The temperature was raised to reach 260° C., at which polymerization was allowed to proceed for 5 hours to obtain a polymer (step (ii)).

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 5.

Example 2

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. Then, polymerization was allowed to proceed until the number average molecular weight reached 6800. Thus, a component (a) was obtained, which was to be used as a hard segment.

To the resultant, 25 g (0.17 mol) of adipic acid as a component (b) was added the amount of which was equivalent to the number of moles of the terminal amine groups contained in the hard segment. Reaction was allowed to proceed at 220° C. for 1 hour for dicarboxylation of the hard segment (step (i)).

Thereto, 103 g (0.172 mol) of a polyether diamine (Jeffamine ED600 manufactured by Huntsman) as a component (c1) was added, the amount of which was equivalent to the total number of moles of the terminal carboxyl groups present on both ends of the dicarboxylated hard segment obtained above. The temperature was raised to reach 260° C., at which polymerization was allowed to proceed for 5 hours to obtain a polymer (step (ii)).

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 2.

Example 3

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. Then, polymerization was allowed to proceed until the number average molecular weight reached 9900. Thus, a component (a) was obtained, which was to be used as a hard segment.

To the resultant, 17.5 g (0.12 mol) of adipic acid as a component (b) was added the amount of which was equivalent to the number of moles of the terminal amine groups contained in the hard segment. Reaction was allowed to proceed at 220° C. for 1 hour for dicarboxylation of the hard segment (step (i)).

Thereto, 72 g (0.117 mol) of a polyether diamine (Jeffamine ED600 manufactured by Huntsman) as a component (c1) was added, the amount of which was equivalent to the total number of moles of the terminal carboxyl groups present on both ends of the dicarboxylated hard segment obtained above. The temperature was raised to reach 260° C., at which polymerization was allowed to proceed for 4 hours to obtain a polymer (step (ii)).

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 2.

Example 4

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. Then, polymerization was allowed to proceed until the number average molecular weight reached 5000. Thus, a component (a) was obtained, which was to be used as a hard segment.

To the resultant, 35 g (0.24 mol) of adipic acid as a component (b) was added the amount of which was equivalent to the number of moles of the terminal amine groups contained in the hard segment. Reaction was allowed to proceed at 220° C. for 1 hour for dicarboxylation of the hard segment (step (i)).

Thereto, 22.3 g (0.19 mol) of hexamethylenediamine as a component (d) and 28.8 g (0.048 mol) of a polyether diamine (Jeffamine ED600 manufactured by Huntsman) as a component (c1) were added, so as to have the total amount equivalent to the total number of moles of the terminal carboxyl groups present on both ends of the dicarboxylated hard segment obtained above. The temperature was raised to reach 260° C., at which polymerization was allowed to proceed for 4 hours to obtain a polymer (step (ii)).

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 2.

Example 5

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. Then, polymerization was allowed to proceed until the number average molecular weight reached 5200. Thus, a component (a) was obtained, which was to be used as a hard segment.

To the resultant, 35 g (0.24 mol) of adipic acid as a component (b) was added the amount of which was equivalent to the number of moles of the terminal amine groups contained in the hard segment. Reaction was allowed to proceed at 220° C. for 1 hour for dicarboxylation of the hard segment (step (i)).

Thereto, 19.5 g (0.17 mol) of hexamethylenediamine as a component (d) and 43.2 g (0.072 mol) of a polyether diamine (Jeffamine ED600 manufactured by Huntsman) as a component (c1) were added, so as to have the total amount equivalent to the total number of moles of the terminal carboxyl groups present on both ends of the dicarboxylated hard segment obtained above. The temperature was raised to reach 260° C., at which polymerization was allowed to proceed for 4 hours to obtain a polymer (step (ii)).

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 2.

Example 6

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. Then, polymerization was allowed to proceed until the number average molecular weight reached 5400. Thus, a component (a) was obtained, which was to be used as a hard segment.

To the resultant, 35 g (0.24 mol) of adipic acid as a component (b) was added the amount of which was equivalent to the number of moles of the terminal amine groups contained in the hard segment. Reaction was allowed to proceed at 220° C. for 1 hour for dicarboxylation of the hard segment (step (i)).

Thereto, 14 g (0.12 mol) of hexamethylenediamine as a component (d) and 72 g (0.12 mol) of a polyether diamine (Jeffamine ED600 manufactured by Huntsman) as a component (c1) were added, so as to have the total amount equivalent to the total number of moles of the terminal carboxyl groups present on both ends of the dicarboxylated hard segment obtained above. The temperature was raised to reach 260° C., at which polymerization was allowed to proceed for 4 hours to obtain a polymer (step (ii)).

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 2.

Example 7

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. Then, polymerization was allowed to proceed until the number average molecular weight reached 5100. Thus, a component (a) was obtained, which was to be used as a hard segment.

To the resultant, 35 g (0.24 mol) of adipic acid as a component (b) was added the amount of which was equivalent to the number of moles of the terminal amine groups contained in the hard segment. Reaction was allowed to proceed at 220° C. for 1 hour for dicarboxylation of the hard segment (step (i)).

Thereto, 8 g (0.069 mol) of hexamethylenediamine as component (d) and 101 g (0.168 mol) of a polyether diamine (Jeffamine ED600 manufactured by Huntsman) as a component (c1) were added, so as to have the total amount equivalent to the total number of moles of the terminal carboxyl groups present on both ends of the dicarboxylated hard segment obtained above. The temperature was raised to reach 260° C., at which polymerization was allowed to proceed for 5 hours to obtain a polymer (step (ii)).

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 2.

Example 8

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. Then, polymerization was allowed to proceed until the number average molecular weight reached 4900. Thus, a component (a) was obtained, which was to be used as a hard segment.

To the resultant, 35 g (0.24 mol) of adipic acid as a component (b) was added the amount of which was equivalent to the number of moles of the terminal amine groups contained in the hard segment. Reaction was allowed to proceed at 220° C. for 1 hour for dicarboxylation of the hard segment (step (i)).

Thereto, 3 g (0.026 mol) of hexamethylenediamine as a component (d) and 130 g (0.217 mol) of a polyether diamine (Jeffamine ED600 manufactured by Huntsman) as a component (c1) were added, so as to have the total amount equivalent to the total number of moles of the terminal carboxyl groups present on both ends of the dicarboxylated hard segment obtained above. The temperature was raised to reach 260° C., at which polymerization was allowed to proceed for 4 hours. Then, the pressure was reduced, at which polymerization was allowed to continue for another 4 hours. Thus, a polymer was obtained (step (ii)).

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 2.

Example 9

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. Then, polymerization was allowed to proceed until the number average molecular weight reached 5100. Thus, a component (a) was obtained, which was to be used as a hard segment.

To the resultant, 48.5 g (0.24 mol) of sebacic acid as a component (b) was added the amount of which was equivalent to the number of moles of the terminal amine groups contained in the hard segment. Reaction was allowed to proceed at 220° C. for 1 hour for dicarboxylation of the hard segment (step (i)).

Thereto, 24 g (0.12 mol) of dodecamethylenediamine as a component (d) and 72 g (0.12 mol) of a polyether diamine (Jeffamine ED600 manufactured by Huntsman) as a component (c1) were added, so as to have the total amount equivalent to the total number of moles of the terminal carboxyl groups present on both ends of the dicarboxylated hard segment obtained above. The temperature was raised to reach 260° C., at which polymerization was allowed to proceed for 4 hours to obtain a polymer (step (ii)).

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 2.

Comparative Example 1

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. Then, polymerization was allowed to proceed until the number average molecular weight reached 2800. Thus, a compound was obtained, which was to be used as a hard segment. GPC evaluation was carried out, which observed peaks attributable to a monomer and a dimer.

To the resultant, 58 g (0.40 mol) of adipic acid was added the amount of which was equivalent to the number of moles of the terminal amine groups contained in the hard segment. Reaction was allowed to proceed at 220° C. for 1 hour for dicarboxylation of the hard segment.

Thereto, 240 g (0.40 mol) of a polyether diamine (Jeffamine ED600 manufactured by Huntsman) was added, the amount of which was equivalent to the total number of moles of the terminal carboxyl groups present on both ends of the dicarboxylated hard segment obtained above. The temperature was raised to reach 260° C., at which polymerization was allowed to proceed for 3 hours. When 3 hours had passed, the melt viscosity stopped increasing. So as to terminate polymerization, stirring was stopped. Thus, a polymer was obtained. A string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 2.

Comparative Example 2

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. Then, polymerization was allowed to proceed until the number average molecular weight reached 12500. Thus, a compound was obtained, which was to be used as a hard segment.

To the resultant, 14.6 g (0.10 mol) of adipic acid was added the amount of which was equivalent to the number of moles of the terminal amine groups contained in the hard segment. Reaction was allowed to proceed at 220° C. for 1 hour for dicarboxylation of the hard segment.

Thereto, 60 g (0.100 mol) of a polyether diamine (Jeffamine ED600 manufactured by Huntsman) was added, so as to have the amount equivalent to the total number of moles of the terminal carboxyl groups present on both ends of the dicarboxylated hard segment obtained above. The temperature was raised to reach 260° C., at which polymerization was allowed to proceed for 4 hours. Thus, a polymer was obtained.

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 2.

Comparative Example 3

To a 3-L reaction vessel equipped with a stirrer, a temperature controller, a pressure gauge, a nitrogen gas inlet, and a condensation water outlet, 1200 g of 12-aminododecanoic acid and 0.6 g of hypophosphorous acid were fed. The interior of the reaction vessel was sufficiently replaced with nitrogen. The temperature was raised to and kept at 280° C. for 1 hour for melting. After the entire content of the vessel had melted, the temperature was decreased to 260° C., at which polymerization was allowed to proceed for 4 hours to obtain a polymer.

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article, which was subjected to a tensile test and also to measurement of Shore (D) hardness. The results are shown in Table 2.

Comparative Example 4

To a 3-L reaction vessel equipped with a stirrer, a temperature controller, a pressure gauge, a nitrogen gas inlet, and a condensation water outlet, 1200 g of 6-aminohexanoic acid and 0.6 g of hypophosphorous acid were fed. To the resulting mixture, the following were added: 35 g (0.24 mol) of adipic acid the amount of which was equivalent to the number of moles of the terminal amine groups present on one end of the resulting hard segment that was assumed to have a number average molecular weight of 5000; and 144 g (0.24 mol) of a polyether diamine (Jeffamine ED600 manufactured by Huntsman) the amount of which was equivalent to the total number of moles of the terminal carboxyl groups present on both ends of the dicarboxylated hard segment. The interior of the reaction vessel was sufficiently replaced with nitrogen. The temperature was raised to and kept at 280° C. for 1 hour for melting. Then, the temperature was decreased to 260° C., at which polymerization was allowed to proceed for 6 hours.

After the completion of the polymerization, stirring was stopped and then a string of colorless transparent polymer in a molten state was pulled out through a discharge port. The resulting string was cooled with water and pelletized to obtain about 1 kg of pellets. The resulting pellets were subjected to measurement of MFR and the number average molecular weight (Mn). The results are shown in Table 2.

The pellets were made into a formed article (specimen), which was subjected to a tensile test and also to measurement of Shore (D) hardness. The results are shown in Table 2.

TABLE 2

| | MFR (g/10 min) | Mn | Shore (D) hardness | Elongation at break (%) | Strength at break (MPa) |
|---|---|---|---|---|---|
| Example 1 | 15.1 | 84000 | 66 | 420 | 73 |
| Example 2 | 14.0 | 58000 | 68 | 404 | 74 |
| Example 3 | 12.0 | 41000 | 70 | 380 | 74 |
| Example 4 | 5.0 | 43226 | 73 | 358 | 70 |
| Example 5 | 6.2 | 47811 | 72 | 360 | 68 |
| Example 6 | 11.9 | 45166 | 70 | 375 | 73 |
| Example 7 | 13.1 | 70862 | 67 | 410 | 68 |
| Example 8 | 14.3 | 78950 | 66 | 430 | 72 |
| Example 9 | 12.0 | 56980 | 67 | 406 | 77 |
| Comparative Example 1 | 30.1 | 45000 | 65 | 346 | 55 |
| Comparative Example 2 | 8.9 | 23000 | 72 | 282 | 61 |
| Comparative Example 3 | 3.2 | 18000 | 74 | 256 | 64 |
| Comparative Example 4 | 17.0 | 71000 | 63 | 279 | 65 |

Each of the polyamide elastomers obtained in Examples 1 to 9 had an MFR value suitable for extrusion molding; was excellent in melt moldability; and was excellent in mechanical properties, such as elongation at break and strength at break, as proven by the tensile test. With these properties in such excellent balance, these polyamide elastomers obtained in the examples are suitable for use in production of medical tubes and balloons. Comparison between the results of the examples and those of the comparative examples has proven that the polyamide elastomers obtained in the examples are superior in elongation at break and strength at break to those obtained in the comparative examples with a similar Shore (D) hardness.

Example 10

A transparent pellet was obtained in the same manner as in Example 3 except that the amount of hypophosphorous acid was changed to 0.13 g (100 ppm). The resulting pellet was subjected to extrusion molding to obtain a tube (parison). The resulting parison was subjected to blow molding to obtain a catheter balloon with a rate of enlargement of the inner diameter of 640%. Table 6 shows the concentration of the element phosphorus, the result of molding procedure, and the result of the pressure resistance test for the molded article. The concentration (100 ppm) of hypophosphorous acid when added was determined based on the total amount of 12-aminododecanoic acid, adipic acid, hexamethylenediamine, and polyether diamine. This manner of determining the concentration of hypophosphorous acid also applies to Example 11.

Example 11

A transparent pellet was obtained in the same manner as in Example 3 except that the amount of hypophosphorous acid was changed to 1.32 g (1000 ppm). The resulting pellet was subjected to extrusion molding to obtain a tube (parison). The resulting parison was subjected to blow molding to obtain a catheter balloon with a rate of enlargement of the inner diameter of 640%. Table 6 shows the concentration of the element phosphorus, the result of molding procedure, and the result of the pressure resistance test for the molded article.

TABLE 3

|  | Concentration of phosphorus compound when added (ppm) | Concentration of element phosphorus in pellet (ppm) | Cracks | Rate of enlargement of inner diameter (%) | Compressive strength (atm) |
|---|---|---|---|---|---|
| Example 10 | 100 | 45 | None | 640 | 22 |
| Example 11 | 1000 | 450 | None | 640 | 21 |

As long as the concentration of the element phosphorus was within the certain range, excellent moldability of a parison into a balloon was obtained with no cracks even at a great rate of enlargement of the inner diameter. This result indicates that the compressive strength has been further enhanced.

The invention claimed is:

1. A polyamide elastomer that is a reaction product of at least components (a), (b), and (c):
   the component (a) being at least one compound represented by formula (1):

$$HOOC-R_1-(-NH-CO-R_1-)_n-NH_2 \quad (1)$$

where each $R_1$ independently represents a linear saturated hydrocarbon group containing 1 or more carbon atoms; n represents a real number of 0 or greater; and when the formula contains two or more types of repeating units each containing $R_1$, n represents a total number of the two or more types of the repeating units each containing $R_1$, the component (a) having a number average molecular weight of 4000 or higher and 10,000 or lower;
   the component (b) being at least one compound represented by formula (2):

$$HOOC-R_2-COOH \quad (2)$$

where $R_2$ represents a direct bond or a linear saturated hydrocarbon group containing 1 or more carbon atoms;
   the component (c) being at least one compound represented by formula (3):

$$H_2N-R_4-(-O-R_4-)_m-NH_2 \quad (3)$$

where each $R_4$ independently represents a saturated hydrocarbon group containing 1 or more carbon atoms; m represents a real number of 1 or greater; and when the formula contains two or more types of repeating units each containing $R_4$, m represents a total number of the two or more types of the repeating units each containing $R_4$, the component (c) having a number average molecular weight of 500 or higher and 700 or lower.

2. The polyamide elastomer according to claim 1 that is a reaction product of at least the components (a) to (c) and a component (d),
   the component (d) being at least one compound represented by formula (4):

$$H_2N-R_3-NH_2 \quad (4)$$

where $R_3$ represents a saturated hydrocarbon group containing 1 or more carbon atoms.

3. The polyamide elastomer according to claim 1 or 2, wherein the component (c) is a component (c1),
   the component (c1) being at least one compound represented by formula (5):

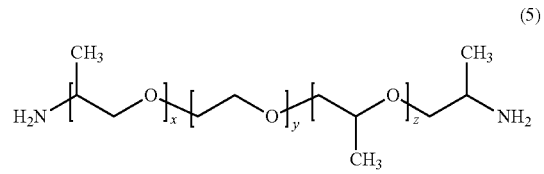

(5)

where (x+z) represents a real number of 1 or greater and 6 or smaller; and y represents a real number of 1 or greater and 20 or smaller.

4. The polyamide elastomer according to claim 1, wherein the component (d) is at least one aliphatic diamine selected from
   ethylenediamine,
   trimethylenediamine,
   tetramethylenediamine,
   hexamethylenediamine,
   undecamethylenediamine,
   dodecamethylenediamine, and
   2,2-4/2,4,4-trimethylhexamethylenediamine.

5. The polyamide elastomer according to claim 1, wherein a molar ratio (A/B) of amino groups in the component (a) (represented by (A)) to monocarboxyl groups in the component (b) (represented by (B)) is substantially 1/1.

6. The polyamide elastomer according to claim 1, comprising a phosphorus compound in a manner of containing element phosphorus in an amount of 5 ppm or higher and 5000 ppm or lower.

7. A medical device comprising a member that is made by using the polyamide elastomer according to claim 1.

8. The medical device according to claim 7, wherein the member is a catheter balloon or a medical tube.

9. A method of producing the polyamide elastomer according to claim 1, the method comprising:
   step (i) of allowing the component (a) and the component (b) to react, thereby obtaining a prepolymer; and
   step (ii) of mixing the prepolymer with the component (c) to react with each other.

10. The method of producing the polyamide elastomer according to claim 9, wherein the prepolymer is mixed with the component (c) and the component (d) to react with each other.

11. The method of producing the polyamide elastomer according to claim 9 or 10, wherein each of the components in at least the steps (i) and (ii) is caused to react by a melt kneading method.

12. The method of producing the polyamide elastomer according to claim 9 or 10, further comprising adding a phosphorus compound in at least one of the steps (i) and (ii) in an amount of 10 ppm or higher and 10000 ppm or lower relative to a total amount of the components (a) to (c) or a total amount of the component (a) to (d).

\* \* \* \* \*